(12) United States Patent
Branch, Jr.

(10) Patent No.: US 7,217,293 B2
(45) Date of Patent: May 15, 2007

(54) EXPANDABLE SPINAL IMPLANT

(75) Inventor: Charles L. Branch, Jr., Advance, NC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 443 days.

(21) Appl. No.: 10/718,770

(22) Filed: Nov. 21, 2003

(65) Prior Publication Data

US 2005/0113916 A1 May 26, 2005

(51) Int. Cl.
*A61F 2/44* (2006.01)

(52) U.S. Cl. .................. 623/17.16; 623/17.11

(58) Field of Classification Search .............. 623/17.16
See application file for complete search history.

(56) References Cited

U.S. PATENT DOCUMENTS

| | | | |
|---|---|---|---|
| 5,059,193 A | 10/1991 | Kuslich | |
| 5,514,180 A | 5/1996 | Heggeness et al. | |
| 5,554,191 A | 9/1996 | Lahille et al. | |
| 5,653,763 A | 8/1997 | Errico et al. | |
| 5,658,335 A | 8/1997 | Allen | |
| 5,665,122 A | 9/1997 | Kambin | |
| 5,749,916 A | 5/1998 | Richelsoph | |
| 5,782,832 A | 7/1998 | Larsen et al. | |
| 5,976,187 A | 11/1999 | Richelsoph | |
| 5,980,522 A | 11/1999 | Koros et al. | |
| 6,102,950 A | 8/2000 | Vaccaro | |
| 6,117,174 A | 9/2000 | Nolan | |
| 6,126,689 A | 10/2000 | Brett | |
| 6,129,763 A | 10/2000 | Chauvin et al. | |
| 6,159,244 A | 12/2000 | Suddaby | |
| 6,174,334 B1 | 1/2001 | Suddaby | |
| 6,176,882 B1 | 1/2001 | Biedermann et al. | |
| 6,183,517 B1 | 2/2001 | Suddaby | |
| 6,193,757 B1 | 2/2001 | Foley et al. | |
| 6,217,579 B1 | 4/2001 | Koros | |
| 6,332,894 B1 | 12/2001 | Salcup et al. | |
| 6,332,895 B1 | 12/2001 | Suddaby | |
| 6,371,989 B1 | 4/2002 | Chauvin et al. | |
| 6,395,031 B1 | 5/2002 | Foley et al. | |
| 2002/0040243 A1* | 4/2002 | Attali et al. ............. | 623/17.16 |
| 2002/0045945 A1* | 4/2002 | Liu et al. ................ | 623/17.16 |
| 2002/0143401 A1 | 10/2002 | Michelson | |

FOREIGN PATENT DOCUMENTS

| | | |
|---|---|---|
| FR | 2 753 368 | 3/1998 |
| WO | WO 00/25706 A | 5/2000 |

\* cited by examiner

*Primary Examiner*—Corrine McDermott
*Assistant Examiner*—Christopher D. Prone
(74) *Attorney, Agent, or Firm*—Krieg DeVault, LLP

(57) ABSTRACT

An expandable spinal implant including a body having a plurality of movable portions cooperating to define an outer cross section having first and second transverse dimensions and first and second substantially planar surfaces disposed generally opposite one another and adapted to engage adjacent vertebral bodies. An expansion member co-acts with the movable portions to expand the body along each of the first and second transverse dimensions.

49 Claims, 4 Drawing Sheets

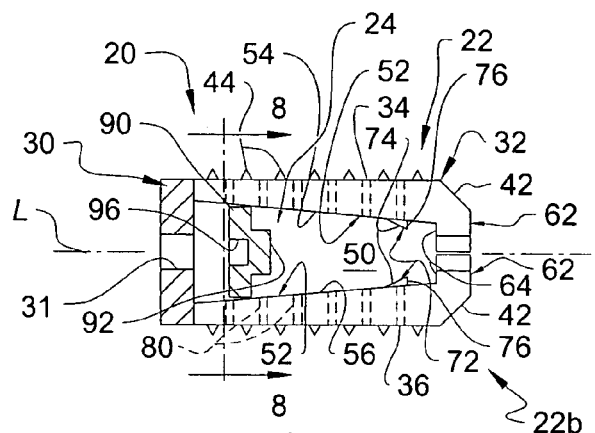
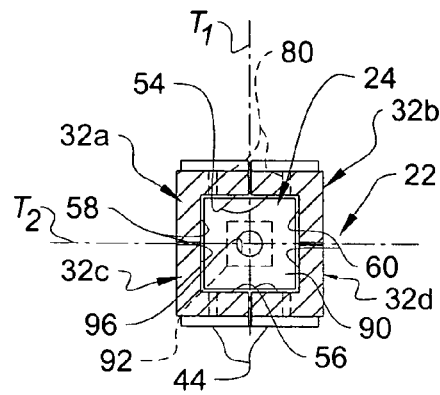
Fig. 7
Fig. 8
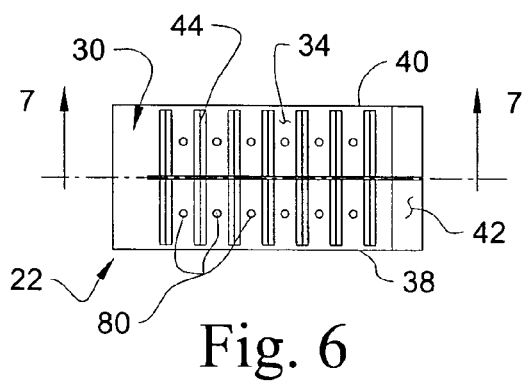
Fig. 6
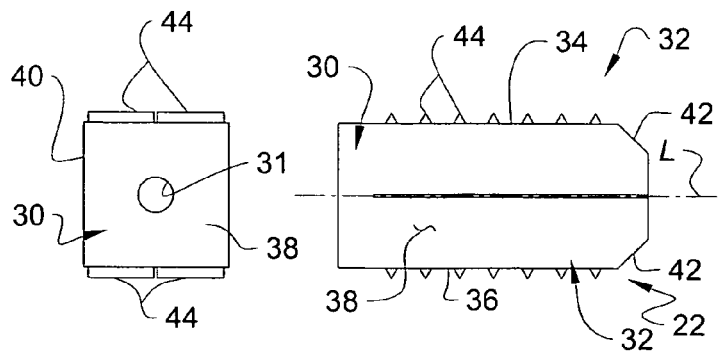
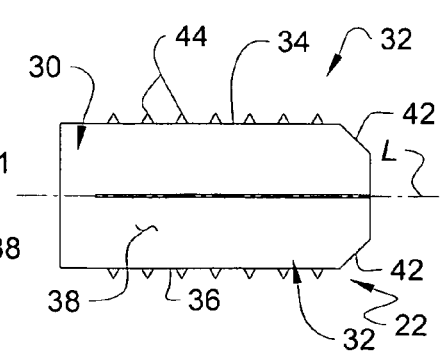
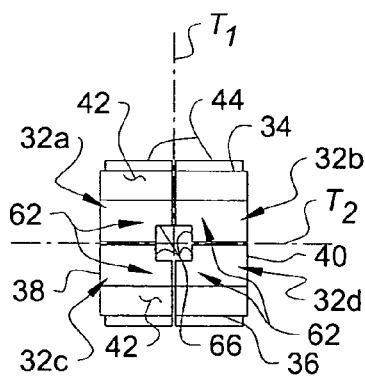
Fig. 4    Fig. 3    Fig. 5

EXPANDABLE SPINAL IMPLANT

FIELD OF THE INVENTION

The present invention relates generally to the field of spinal implants, and more particularly relates to an expandable spinal implant.

BACKGROUND

There have been numerous attempts to develop an intervertebral implant to replace a damaged or degenerated natural spinal disc and to maintain sufficient stability of the disc space between adjacent vertebrae, at least until arthrodesis is achieved. These types of intervertebral implants have taken many forms.

For example, one of the more prevalent designs includes spinal implants having a cylindrical shape. With regard to cylindrically-shaped implants, the exterior portion of the implant is typically threaded to facilitate insertion into the disc space. Additionally, intervertebral implants can either be solid, sometimes referred to as a spacer or plug, or can define a hollow interior designed to permit bone in-growth, sometimes referred to as a fusion device or fusion cage. The interior of a fusion device may be filled with a bone growth inducing substance to facilitate or promote bone growth into and through the device. It is commonly accepted that intervertebral implants that facilitate or promote natural bone in-growth typically achieve a more rapid and stable arthrodesis.

One area that is usually not addressed by the above-discussed intervertebral implant designs concerns maintaining and restoring the natural anatomy of the fused spinal segment. Notably, once natural disc material is removed, the normal lordotic or kyphotic curvature of the spine is reduced or eliminated. With regard to prior implants having a substantially uniform outer cross section, the need to restore this curvature is largely neglected. Moreover, in some cases the adjacent vertebral bodies are reamed to form a passage having a shape corresponding to the particular shape of the implant. In other cases, the normal curvature is established prior to reaming followed by insertion of the implant. However, these techniques generally involve over-reaming of the posterior portion of the adjacent vertebral bodies, thereby resulting in excessive removal of load bearing vertebral bone which may lead to instability of the portion of the spinal column being treated. Also, it is typically difficult to ream through the posterior portion of the lower lumbar segment where lordosis is the greatest.

Accordingly, with regard to many intervertebral implant designs, limited effort or no effort is made to restore the lordotic curvature. As a result, the implant is likely to cause a kyphotic deformity as the vertebral bodies settles around the intervertebral implant. Additionally, with regard to intervertebral implants that attempt to restore the lordotic curvature, expansion of the implant is typically limited to a single direction along the height of the disc space, with no consideration being given to expanding the implant in a lateral direction to provide a larger overall area for absorbing/distributing vertebral loads and improved stability and/or an increased resistance to subsidence into the adjacent vertebral bodies.

Thus, there is a general need in the industry to provide an improved expandable spinal implant. The present invention satisfies this need and provides other benefits and advantages in a novel and unobvious manner.

SUMMARY

The present invention relates generally to an expandable spinal implant. While the actual nature of the invention covered herein can only be determined with reference to the claims appended hereto, certain forms of the invention that are characteristic of the preferred embodiments disclosed herein are described briefly as follows.

In one form of the present invention, an expandable spinal implant is provided, including a body having a plurality of movable portions cooperating to define an outer cross section having a first transverse dimension and a second transverse dimension and defining first and second substantially planar surfaces disposed generally opposite one another and adapted to engage adjacent vertebral bodies. The spinal implant also includes an expansion member co-acting with the movable portions to expand the outer cross section along the first and second transverse dimensions.

In another form of the present invention, an expandable spinal implant is provided, including a body having a longitudinal axis and a plurality of movable portions cooperating to define a generally rectangular outer cross section having a first transverse dimension and a second transverse dimension. The spinal implant also includes an expansion member co-acting with the movable portions to expand the outer cross section along the first and second transverse dimensions.

In another form of the present invention, an expandable spinal implant is provided, including a body having a longitudinal axis and a plurality of movable portions cooperating to define an outer cross section having a first transverse dimension and a second transverse dimension, with the movable portions having substantially planar inner surfaces that cooperate to define an inner chamber having a substantially rectangular inner cross section and with the inner surfaces defining an inward taper along the longitudinal axis. The spinal implant also includes an expansion member having a substantially rectangular outer cross section and engaging the inner surfaces of the movable portions to expand the movable portions along the first and second transverse dimensions as the expansion member is displaced generally along the longitudinal axis.

In another form of the present invention, an expandable spinal implant is provided, including a body having a longitudinal axis and including a plurality of movable portions cooperating to define an outer cross section having a first transverse dimension and a second transverse dimension and defining first and second substantially planar surfaces disposed generally opposite one another and adapted to engage adjacent vertebral bodies. The spinal implant also includes means for expanding the outer cross section along the first and second transverse dimensions.

In another form of the present invention, a surgical method is provided, including providing an expandable spinal implant having a plurality of movable portions extending along a longitudinal axis and cooperating to define an outer cross section having a first transverse dimension and a second transverse dimension, with the movable portions defining first and second substantially planar surfaces disposed generally opposite one another. The method further includes inserting the spinal implant within an intervertebral space with the first and second substantially planar surfaces positioned adjacent first and second vertebrae, and expanding the outer cross section along each of the first and second transverse dimensions.

It is one object of the present invention to provide an improved expandable spinal implant. Further objects, features, advantages, benefits, and aspects of the present invention will become apparent from the drawings and description contained herein.

BRIEF DESCRIPTION OF THE DRAWINGS

FIG. 3 is a side view of the spinal implant illustrated in FIG. 1.

FIG. 4 is a proximal end view of the spinal implant illustrated in FIG. 1.

FIG. 5 is a distal end view of the spinal implant illustrated in FIG. 1.

FIG. 6 is a top plan view of the spinal implant illustrated in FIG. 1.

FIG. 7 is a cross-sectional side view of the spinal implant illustrated in FIG. 6, as viewed along line 7—7 of FIG. 6.

FIG. 8 is a cross-sectional view of the spinal implant illustrated in FIG. 7, as viewed along line 8—8 of FIG. 7.

DESCRIPTION OF THE PREFERRED EMBODIMENTS

Figure 1:
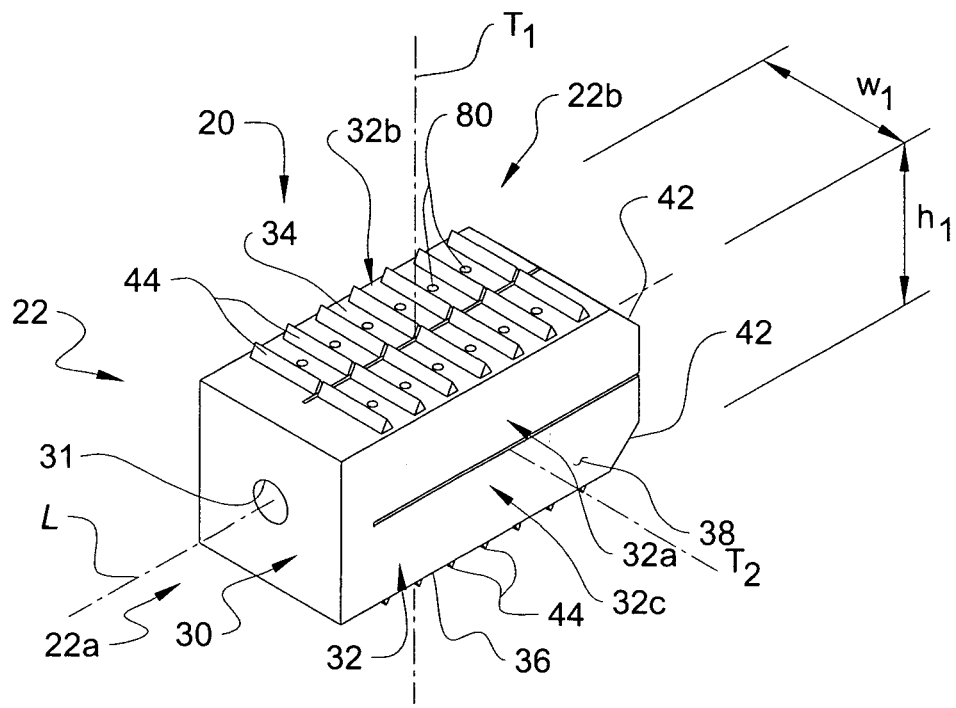
FIG. 1 is a perspective end view of an expandable spinal implant according to one form of the present invention, as shown in a non-expanded configuration.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 2:
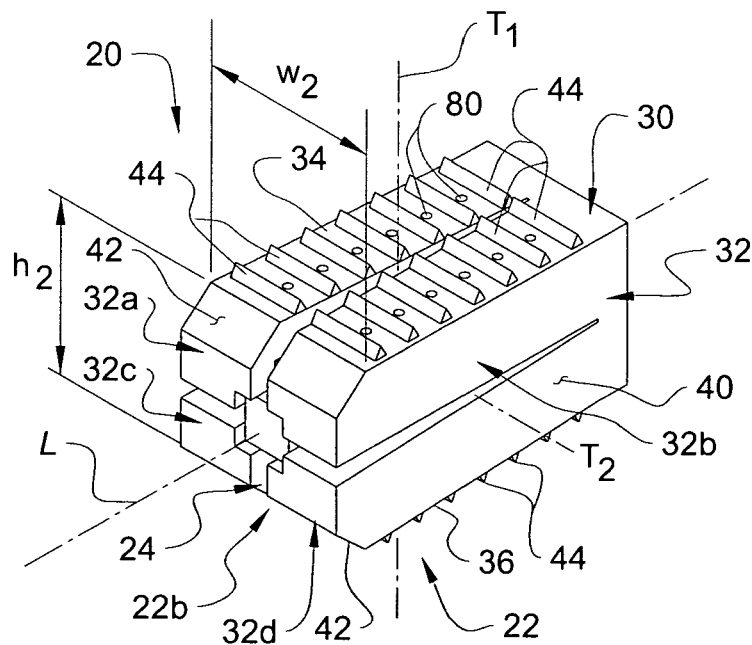
FIG. 2 is a perspective end view of the spinal implant illustrated in FIG. 1, as shown in an expanded configuration.

Referring to FIGS. 1–8, shown therein is a spinal implant 20 according to one form of the present invention. The spinal implant 20 extends along a longitudinal axis L and is generally comprised of an expandable fusion cage 22 and an expansion member 24. As will be discussed below, the expansion member 24 serves to transition the fusion cage 22 from an initial configuration, as shown in FIG. 1, toward an expanded configuration, as shown in FIG. 2.

In the illustrated embodiment of the invention, expansion of the fusion cage 22 occurs along two transverse dimensions (i.e., along dimensions that are transverse to the longitudinal axis L), and more specifically along a first transverse axis $T_1$ and a second transverse axis $T_2$. However, it should be understood that in other embodiments of the invention, expansion of the fusion cage 22 may occur along any number of axes, including a single transverse axis or three or more transverse axes. As will be discussed in greater detail below, in the illustrated embodiment of the invention, the fusion cage 22 is configured to expand along the first transverse axis $T_1$ to distract the disc space and/or to restore/maintain lordosis between the adjacent vertebral bodies. Additionally, the fusion cage 22 is configured to expand along the second transverse axis $T_2$ to distribute loading of the fusion cage 22 across a larger and more dispersed area of the adjacent vertebral endplates to provide improved stability and/or an increased resistance to subsidence.

The components of the spinal implant 20 are preferably formed of a bio-compatible material. In one embodiment, the fusion cage 22 and/or the expansion member 24 are formed of a material that has a modulus of elasticity substantially similar to that of bone. In a further embodiment; the fusion cage 22 and/or the expansion member 24 are formed of a resorbable material that resorbs or degrades within the body over a period of time for partial or total replacement by bone. In a specific embodiment of the invention, the fusion cage 22 and/or the expansion member 24 are formed of a polymeric material, including, for example, a non-resorbable polymer such as polyetheretherketone (PEEK) or a resorbable polymers such as polylactates (PLA). However, it should be understood that other suitable polymeric/non-polymeric materials and/or other suitable resorbable/non-resorbable materials are also contemplated for use in association with the present invention. Examples of other suitable materials include composite polymers, non-reinforced polymers, carbon-reinforced polymer composites, carbon fiber, PMMA, calcium hydroxide, ceramics, polylactide, polyglycolide, tyrosine-derived polycarbonate, polyanhydride, polyorthoester, polyphosphazene, calcium phosphate, calcium hydroxide, hydroxyapatite, bioactive glass, or any combination thereof. The use of metallic materials are also contemplated, including, for example, stainless steel and stainless steel alloys, titanium and titanium alloys, shape-memory alloys, cobalt chrome alloys, or any combination thereof. Additionally, the use of bone or bone substitute materials is also contemplated.

In one aspect of the invention, the fusion cage 22 is comprised of a fixed base portion 30 and plurality of movable branch portions 32 extending from the fixed base portion 30 generally along the longitudinal axis L. In the illustrated embodiment of the invention, the fixed base portion 30 includes an opening 31 extending therethrough and positioned generally along the longitudinal axis L adjacent the proximal end 22a of the fusion cage, the purpose of which will be discussed below. Additionally, in the illustrated embodiment, the fusion cage 22 includes four movable branch portions 32, including a pair of upper branch portions 32a, 32b and a pair of lower branch portions 32c, 32d. However, it should be understood that the fusion cage 22 may define any number of movable branch portions 32, including two, three, or five or more movable branch portions 32.

The branch portions 32 are coupled to the base portion 30 in such a manner as to allow the branch portions 32 to move relative to one another to provide for expansion of the fusion cage 22. In the illustrated embodiment of the invention, the branch portions 32 are formed integral with the base portion 30 to define a single-piece, unitary fusion cage 22. As such, the base portion 30 flexibly interconnects the branch portions 32 in a manner allowing expansion of the fusion cage 22 via flexible material deformation of the branch portions 32 and/or the base portion 30. The interconnection between the base portion 30 and the branch portions 32 acts in a hinge-like manner during expansion of the fusion cage 22 to provide for substantially independent movement of the branch portions 32.

Although the illustrated embodiment of the fusion cage 22 utilizes integrally connected branch portions 32, it is also contemplated that the branch portions 32 may be formed separately and connected together to form a multi-piece fusion cage assembly. In another alternate embodiment, the branch portions 32 may be pivotally attached to the base portion 30 or directly to one other via a hinge or pivot pin such that the fusion cage 22 may be expanded without flexible material deformation. Other suitable means for coupling the branch portions 32 together to provide for expansion of the fusion cage 22 are also contemplated, including forming or coupling of the branch portions 32 directly to one another without the use of a fixed base portion 30.

In a further aspect of the invention, the movable branch portions 32 cooperate with one another to define a generally rectangular outer transverse cross section. In one embodiment, the fusion cage 22 includes a first pair of substantially planar upper and lower surfaces 34, 36 extending generally along the second transverse axis $T_2$ (defined by branch portions 32a, 32b and 32c, 32d, respectively) and a second pair of substantially planar side surfaces 38, 40 extending along the first transverse axis $T_1$ (defined by branch portions 32a, 32c and 32b, 32d, respectively). In a further embodiment, the fusion cage 22 has a substantially parallelpiped configuration including six sides, with each side generally defining a parallelogram. However, it should be understood that other shapes, configurations and outer cross sections of the branch portions 32 and the fusion cage 22 are also contemplated as falling within the scope of the present invention.

In another embodiment of the invention, the upper and lower corners of the fusion cage 22 adjacent the distal end 22b are tapered or beveled to facilitate insertion of the fusion cage 22 into an intervertebral disc space and/or distraction of the adjacent vertebral bodies $V_U$, $V_L$. Specifically, the distal end portions of the upper pair of branches 32a, 32b define an inwardly tapering surface 42 extending from the upper surface 34 toward the distal end 22b of the fusion cage 22. Similarly, the distal end portions of the lower pair of branches 32c, 32d define an inwardly tapering surface 42 extending from the lower surface 36 toward the distal end 22b of the fusion cage 22. The tapered surfaces 42 may be particularly useful to facilitate insertion of the fusion cage 22 between the adjacent vertebral bodies $V_U$, $V_L$ via an impaction or push-in technique. Although not specifically illustrated in the figures, it should be understood that the side or lateral corners of the fusion cage 22 defined by the branches 32a, 32c and 32b, 32d, respectively, may also be beveled to define an inwardly tapering surface extending from the side surfaces 38, 40 toward the distal end 22b of the fusion cage 22.

In a further embodiment of the invention, the upper and lower surfaces 34, 36 defined by the branch portions 32a, 32b and 32c, 32d, respectively, define a number of bone anchoring elements 44 adapted for engagement with adjacent vertebral bodies $V_U$, $V_L$ (FIGS. 9 and 10) to prevent or inhibit movement of the fusion cage 22 once implanted within the intervertebral disc space. In a specific embodiment, the bone anchoring elements 44 comprise a number of rows of triangular-shaped ridges or teeth extending across a width of the fusion cage 22 generally along the transverse axis $T_2$. However, it should be understood that other shapes, orientations and/or configurations of ridges or teeth are also contemplated as falling within the scope of the present invention. It should also be understood that other configurations of bone anchoring elements 44 are also contemplated for use in association with the fusion cage 22, such as, for example, other types of projections extending from the upper and lower surfaces 34, 36 of the fusion cage, including spikes, surface roughening, or threads. It should further be understood that in other embodiments of the invention, the upper and lower surfaces 34, 36 of the fusion cage 22 need not necessarily include bone anchoring elements 44, but may alternatively define a substantially smooth configuration devoid of any surface projections or irregularities. In other embodiments of the invention, the side surfaces 38, 40 of the fusion cage 22 may also define bone anchoring elements in instances where the side surfaces 38, 40 may at some point be in full or partial engagement with the adjacent vertebral bodies $V_U$, $V_L$.

As illustrated in FIG. 2, upon transitioning of the fusion cage 22 toward an expanded configuration, the upper branch portions 32a, 32b will separate or splay apart relative to the lower branch portion 32c, 32d to expand the fusion cage 22 along the first transverse axis $T_1$. Similarly, the upper branch portions 32a, 32b will separate or splay apart relative to one another and the lower branch portion 32c, 32d will separate or splay apart relative to one another to expand the fusion cage 22 along the second transverse axis $T_2$. As a result, the fusion cage 22 is capable of expanding along two transverse dimensions. In one embodiment of the invention, the transverse dimensions correspond to an axial/vertical dimension of the disc space (e.g., the height of the disc space) and a lateral/horizontal dimension of the disc space (e.g., the width or depth of the disc space).

In the illustrated embodiment of the invention, since the movable branch portions 32 are integrally connected with the base portion 30, expansion of the fusion cage 22 is not uniform along the longitudinal axis L. Instead, the fixed proximal ends of the branch portions 32 adjacent the base portion 30 remain relatively stationary and therefore do not appreciably expand along the transverse axes $T_1$, $T_2$. However, the movable distal ends of the branch portions 32 separate or splay apart to expand the distal end portion of the fusion cage 22 from an initial height $h_1$ and width $w_1$ (FIG. 1) to an expanded height $h_2$ and width $w_2$ (FIG. 2). In one embodiment, expansion of the fusion cage 22 along the transverse axis $T_1$ (the change in height between $h_1$ and $h_2$) and along the transverse axis $T_2$ (the change in width between $w_1$ and $w_2$) falls within a range of about 2–4 millimeters. However, it should be understood that other embodiments of the invention are also contemplated wherein the fusion cage 22 is configured to expand less than 2 millimeters or greater than 4 millimeters along the transverse axes $T_1$ and $T_2$. In a specific embodiment of the invention, the initial height $h_1$ and width $w_1$ of the fusion cage 22 are each about 10 millimeters, and the expanded height $h_2$ and width $w_2$ of the fusion cage 22 are each about 14 millimeters. However, it should be understood that these specific dimensions are exemplary, and that other dimensions of the fusion cage 22 are also contemplated.

In the illustrated embodiment of the invention, the initial height $h_1$ and width $w_1$ of the fusion cage 22 are substantially equal, thereby providing the fusion cage 22 with an initial configuration having a square-shaped transverse cross section. Likewise, the expanded height $h_2$ and width $w_2$ of the fusion cage 22 are also illustrated as being substantially equal, thereby providing the fusion cage 22 with an expanded configuration adjacent the distal end 22b having a square-shaped transverse cross section. It should be understood, however, that in other embodiments of the invention, the initial height $h_1$ and width $w_1$ of the fusion cage 22 and/or the expanded height $h_2$ and width $w_2$ of the fusion cage 22 may differ. It should also be understood that the rate of expansion along the transverse axes $T_1$ and $T_2$ need not necessarily be equal. Instead, the fusion cage 22 and/or the expansion member 24 may be configured to provide unequal or varying rates of expansion along the transverse axes $T_1$ and $T_2$. Additionally, although the illustrated embodiment of the spinal implant 20 is configured to expand the fusion cage 22 in a non-uniform manner along the longitudinal axis L, it is also contemplated that the branch portions 32 may be interconnected in a manner that would allow for relatively uniform expansion of the fusion cage 22 along the longitudinal axis L, or other types of non-uniform expansion of the fusion cage 22, such as, for example, configurations resulting in a greater degree of expansion along the central region of the branch portions 32.

In the illustrated embodiment of the invention, the branch portions 32 have a shell-like configuration and cooperate with one another to define a hollow interior chamber 50 (FIG. 7) extending generally along the longitudinal axis L. In one embodiment, the chamber 50 is sized and configured to receive the expansion member 24 therein such that movement of the expansion member 24 within the chamber 50 engages the expansion member 24 with the branch portions 32 to expand the fusion cage 22 along the first and second transverse axes $T_1$ and $T_2$. In one embodiment, axial displacement of the expansion member 24 generally along the longitudinal axis L causes the branch portions 32 to separate or splay apart, thereby transitioning the fusion cage 22 toward an expanded configuration. However, it should be understood that in other embodiments of the invention, relative rotational or pivotal displacement of the expansion member 24 may cause the branch portions 32 to separate or splay apart to expand the fusion cage 22. Additionally, other types of relative displacement of the expansion member 24 are also contemplated for use in association with the present invention to expand the fusion cage 22, including displacement of the expansion member 24 in directions transverse to the longitudinal axis L.

As illustrated in FIGS. 7 and 8, the branch portions 32 define inner surfaces 52 that cooperate to define the interior chamber 50. In the illustrated embodiment of the invention, the inner surfaces 52 are substantially planar so as to provide the chamber 50 with a generally rectangular inner cross section that corresponds to the outer cross section of the expansion member 24 (FIG. 8). As illustrated in FIG. 8, in one embodiment, the branch portions 32 cooperate to define a first pair of substantially planar upper and lower surfaces 54, 56 (defined by branch portions 32a, 32b and 32c, 32d, respectively) and a second pair of substantially planar side surfaces 58, 60 (defined by branch portions 32a, 32c and 32b, 32d, respectively). As illustrated in FIG. 7, the upper and lower surfaces 54, 56 and the side surfaces 58, 60 (not shown) are inclined or inwardly tapered along the longitudinal axis L to facilitate expansion of the fusion cage 22 along both of the transverse axes $T_1$ and $T_2$, the details of which will be discussed below. However, it should be understood that other shapes, configurations and cross sections of the branch portions 32 and the fusion cage 22 are also contemplated as falling within the scope of the present invention.

In a further embodiment of the invention, one or more of the branch portions 32 defines an inwardly extending flange or transverse projection 62 adjacent the distal end 22b of the fusion cage 22 (FIGS. 5 and 7). In the illustrated embodiment, the branch portions 32a–32d each define an inwardly extending flange or transverse projection 62 that cooperate with one another to define a transverse shoulder 64 extending about the inner periphery of the chamber 50. Additionally, as illustrated in FIG. 5, the inwardly extending corners of each of the transverse flanges 62 each define a cut-out or notch 66, the purpose of which will be discussed below. In the illustrated embodiment, the notch 66 has a rectangular configuration; however, other suitable shapes and configurations are also contemplated as falling with the scope of the present invention.

Figure 10:
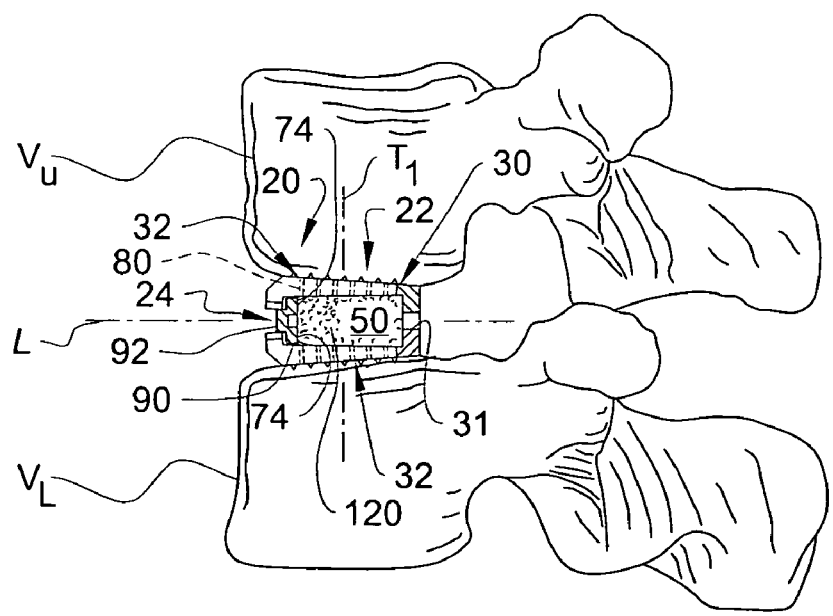
FIG. 10 is a partial cross-sectional side view of the spinal implant illustrated in FIG. 1, as positioned between adjacent vertebral bodies in a fully-expanded configuration.

In another embodiment of the invention, one or more of the branch portions 32 defines a retention element 72 extending from the inner surface 52 adjacent the distal end 22b of the fusion cage 22 (FIG. 7). The retention element 72 is adapted to engage and retain the expansion member 24 in a select position and orientation relative to the branch portions 32 upon expansion of the fusion cage 22 (FIG. 10). In one embodiment, each of the branch portions 32a–32d includes a retention element 72 so as to define a peripheral retention element extending generally about the interior chamber 50. In the illustrated embodiment of the invention, the retention elements 72 are configured as transverse projections or ridges extending from the inner surfaces 52 of the branch portions 32 in a direction transverse to the longitudinal axis L. In a specific embodiment, the retention elements 72 have a triangular configuration, including an inclined or ramped portion 74 tapering inwardly along the longitudinal axis L and a transverse shoulder portion 76 facing generally opposite the shoulder portion 64 defined by the distal end portions of the branches 32a–32d. However, other suitable shapes and configurations of the retention elements 72 are also contemplated as falling with the scope of the present invention. Additional details regarding interaction between the retention element 72 and the expansion member 24 will be discussed below.

In one embodiment of the invention, the branch portions 32 define a number of bone in-growth openings 80 extending through the upper and lower outer surfaces 34, 36 and communicating with the inner chamber 50 to permit bone growth from the adjacent vertebral bodies into and possibly through the fusion cage 22. In one embodiment, the bone in-growth openings 80 are disposed along substantially the entire length of the interior chamber 50 and positioned intermediate the rows of triangular-shaped ridges or teeth 44. Although the bone in-growth openings 80 are illustrated as having a circular cross section defining a relatively small diameter, it should be understood that other shapes, sizes and/or configurations of the bone in-growth openings are also contemplated. For example, in other embodiments of the invention, the bone in-growth openings 80 may have a larger diameter or an elongate slotted configuration. Additionally, although the bone in-growth openings 80 are illustrated as extending through respective ones of the branch portions 32, in other embodiments of the invention, one or more of the openings 80 may be defined between the adjacent branches 32a, 32b and 32c, 32d. Moreover, although the bone in-growth openings 80 are illustrated as extending through the upper and lower outer surfaces 34, 36, it should be understood that bone in-growth openings may also extend through the side surfaces 38, 40 of the fusion cage 22. It should further be understood that although the bone in-growth openings 80 are illustrated and described as communicating with the interior chamber 50, in other embodiments, the openings 80 need not necessarily extend entirely through the branch portions 32.

Referring to FIGS. 7 and 8, shown therein is the expansion member 24 disposed within the interior chamber 50 of the fusion cage 22. The expansion member 24 includes a main body portion 90 and a stem portion 92 extending axially therefrom. Although a specific embodiment of the expansion member 24 is illustrated and described herein, it should be understood that other suitable configurations of the expansion member 24 are also contemplated as falling within the scope of the present invention.

In the illustrated embodiment of the expansion member 24, the main body portion 90 has a generally rectangular outer cross section that substantially corresponds to the inner rectangular cross section of the inner fusion chamber 50. The main body portion 90 includes outer surfaces that are adapted to slide along the inclined inner surfaces 52 of the branch portions 32 during axial displacement of the expansion member 24 along the interior chamber 50 to transition the fusion cage 22 to an expanded configuration. In one embodiment of the invention, the outer surfaces of the main body portion 90 are substantially planar and are arranged generally parallel with the longitudinal axis L. However, other shapes, configurations and outer cross sections of the main body portion 90 are also contemplated for use in association with the present invention. The main body portion 90 also defines an opening 96 sized and configured to receive a distal end portion of a surgical instrument therein to facilitate axial displacement of the expansion member 24 along the inner chamber 50 of the fusion cage 22. In the illustrated embodiment, the tool receiving opening 96 has a generally circular inner cross section to receive a correspondingly shaped distal end portion of a surgical instrument therein. However, other shapes and configurations of the opening 96 are also contemplated for use in association with the present invention, such as, for example, rectangular or hexagonal configurations.

In the illustrated embodiment of the expansion member 24, the stem portion 92 is sized and shaped for positioning within the cut-out or notched portions 66 defined by the distal transverse flanges 62 of the movable branches 32a–32d when the expansion member 24 is disposed adjacent the distal end 22b of the fusion cage 22 (FIG. 10). In one embodiment, the stem portion 92 has a generally rectangular outer cross section; however, other shapes and configurations of the stem portion 92 are also contemplated for use in association with the present invention, such as, for example, hexagonal or circular configurations.

Figure 9:
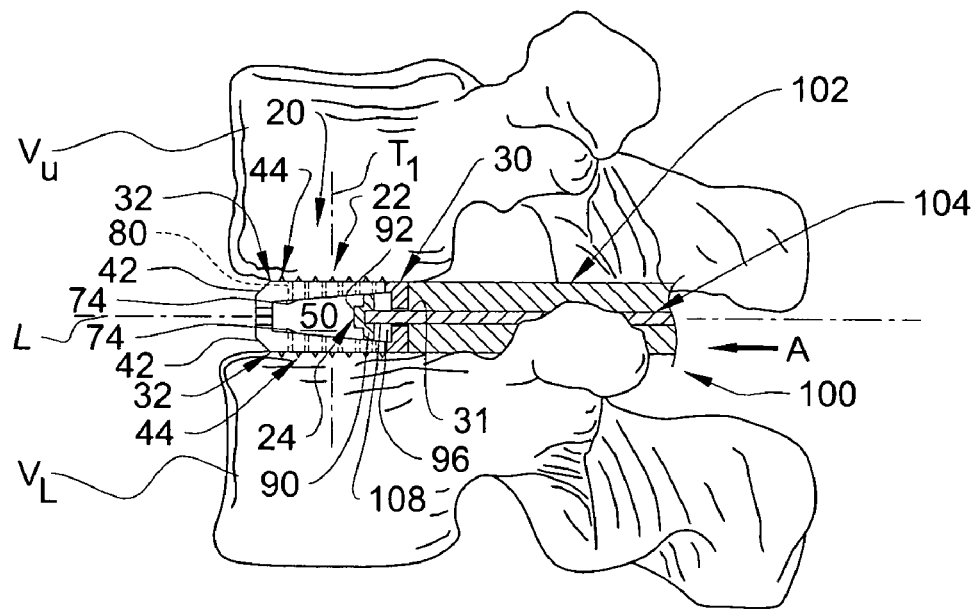
FIG. 9 is a partial cross-sectional side view of the spinal implant illustrated in FIG. 1, as positioned between adjacent vertebral bodies in a non-expanded configuration and with a surgical instrument engaged thereto.

Referring now to FIG. 9, shown therein is a surgical instrument 100 engaged with the implant 20 for transitioning the fusion cage 22 to an expanded configuration. In one embodiment of the invention, the surgical instrument 100 generally includes an outer sleeve 102 and an inner drive shaft 104. The surgical instrument 100 may also include a handle (not shown) to aid in the manipulation and handling of the spinal implant 20. However, it should be understood that other suitable types and configurations of surgical instruments are also contemplated for use in association with the present invention, and that the elements and operation thereof may differ from the embodiment of the surgical instrument 100 illustrated and described herein. For example, another type of instrument that may be used in association with the present invention is illustrated and described in U.S. Pat. No. 6,436,140 to Liu et al., the entire contents of which are hereby incorporated herein by reference.

The outer sleeve 102 of the surgical instrument 100 has a distal end portion that is adapted to engage the fusion cage 22. In one embodiment, engagement between the distal end portion of the sleeve 102 and the fusion cage 22 is abutting engagement. However, it should be understood that other types of engagement are also contemplated, such as, for example, threaded engagement, keyed engagement, tongue-and-groove engagement, frictional engagement, or any other suitable method of engagement. The inner drive shaft 104 is disposed within the outer sleeve 102 and extends through the aperture 31 in the base portion 30 of the fusion cage 22 and into engagement with the expansion member 24. In one embodiment of the invention, engagement between the distal end portion of the drive shaft 104 and the expansion member 24 is abutting engagement. However, other types of engagement are also contemplated, such as, for example, threaded engagement, keyed engagement, tongue-and-groove engagement, frictional engagement, or any other suitable method of engagement. In a further embodiment of the invention, the distal end portion of the drive shaft 104 is configured to be received within the opening 96 in the expansion member 24. In the illustrated embodiment, the distal tip portion 108 of the drive shaft 104 has a generally circular outer cross section that corresponds with the inner cross section of the opening 96 to provide secure engagement between the drive shaft 104 and the expansion member 24. However, other shapes and configurations of the distal tip portion 108 are also contemplated for use in association with the present invention, including rectangular or hexagonal shapes.

As should be appreciated, axial displacement of the drive shaft 104 in the direction of arrow A will correspondingly axially displace the expansion member 24 through the inner chamber 50 to thereby transition the fusion cage 22 toward the fully expanded configuration illustrated in FIG. 10. In one embodiment, the drive shaft 104 may be displaced via threading engagement between the drive shaft 104 and the aperture 31 extending through the fixed base portion 30 of the fusion cage 22. In this manner, rotational movement of the drive shaft 104 and threading engagement with the aperture 31 results in axial movement of the drive shaft 104 generally along the longitudinal axis L in the direction of arrow A. In another embodiment, threading engagement between the inner drive shaft 104 and the outer sleeve 102 may be used to displace the drive shaft 104 generally along the longitudinal axis L in the direction of arrow A. Other suitable techniques for axially displacing the drive shaft 104 are also contemplated as falling within the scope of the present invention.

As discussed above, the outer surfaces of the expansion member 24 slidably engage the inclined inner surfaces 52 of the branch portions 32 as the expansion member 24 is axially displaced along the inner chamber 50 of the fusion cage 22. As should be appreciated, sliding engagement of the expansion member 24 along the inclined surfaces 54, 56, 58 and 60 (FIG. 8) causes the branch portions 32a–32d to separate or splay apart along each of the transverse axes $T_1$ and $T_2$ to transition the fusion cage 22 from the initial configuration illustrated in FIGS. 1 and 9 toward the fully expanded configuration illustrated in FIGS. 2 and 10. As the expansion member 24 is slidably displaced along the upper and lower inclined surfaces 54, 56, the upper and lower outer surfaces 34, 36 of the fusion cage 22 are displaced away from another along the transverse axis $T_1$ to distract the intervertebral disc space and/or to restore/maintain lordosis between the upper and lower vertebrae $V_U$, $V_L$. Likewise, as the expansion member 24 is slidably displaced along the inclined side surfaces 58, 60, the outer side surfaces 38, 40 of the fusion cage 22 are displaced away from another along the transverse axis $T_2$. In this manner, the loads transferred from the upper and lower vertebrae $V_U$, $V_L$ to the fusion cage 22 are distributed across a larger and more dispersed area of the adjacent vertebral endplates to provide improved stability and/or an increased resistance to subsidence.

As the expansion member 24 is advanced to a position adjacent the distal end portion 22b of the fusion cage 22, the expansion member 24 will engage the retention element 74. Specifically, the expansion member 24 will slide along the ramp portions 74 of the retention element 72 and will ultimately be positioned beyond the retention element 72 between the transverse shoulders 64 and 76 defined by the branch portions 32a–32d and the retention element 72, respectively (FIG. 7). As illustrated in FIG. 10, the main body portion 90 of the expansion member 24 is captured between the transverse shoulders 64, 76 to secure the expansion member 24 in the proper orientation and position within the inner chamber 50 and to maintain the fusion cage 22 in the expanded configuration. As also illustrated in FIG. 10, the stem portion 92 of the expansion member 24 is positioned within the cut-out portions 66 defined by the transverse flanges 62a–62b of the branch portions 32a–32d. Engagement of the stem portion 92 with the transverse flanges 62a–62d provides stability between the expansion member 24 and the fusion cage 22 and also provides added support to the distal ends of the branch portions 32.

Following expansion of the fusion cage 22, the surgical instrument 100 may be disengaged from the spinal implant 20 and removed from the patient. In a further embodiment of the invention, a bone growth promoting material 120 (FIG. 10) may be loaded into the inner chamber 50 of the fusion cage 22 to facilitate or promote bone growth from the upper and lower vertebrae $V_U$, $V_L$, through the openings 80 and into and possibly through the fusion cage 22. In one embodiment, the bone growth promoting material 120 is comprised of a bone graft material, a bone morphogenic protein (BMP), or any other suitable bone growth promoting material or substance including but not limited to bone chips or bone marrow, a demineralized bone matrix (DBM), mesenchymal stem cells, and/or a LIM mineralization protein (LMP). It should be understood that the bone growth promoting material 120 can be used with or without a suitable carrier.

In one embodiment, the bone growth promoting material 120 is injected into the inner chamber 50 via the aperture 31 extending through the fixed base portion 30. In another embodiment, the bone growth promoting material 120 is positioned within the inner chamber 50 subsequent to expansion of the fusion cage 22. However, it should be understood that the fusion cage 22 and the expansion member 24 may alternatively be configured so as to allow the bone growth promoting material 120 to be loaded within the inner chamber 50 in another manner and/or prior to or during expansion of the fusion cage 22.

Having illustrated and described the elements and operation of the spinal implant 20, reference will now be made to a technique for implanting the spinal implant 20 within an intervertebral space according to one embodiment of the invention. However, it should be understood that other implantation techniques and procedures are also contemplated, and that the following technique in no way limits the scope of the present invention.

Referring to FIGS. 9 and 10, the vertebral level to be treated is identified, followed by the removal of at least a portion of the natural intervertebral disc via a total or partial discectomy. The endplates of the upper and lower vertebrae $V_U$, $V_L$ are then prepared using known surgical instruments and techniques (e.g., rotating cutters, curettes, chisels, etc.). Notably, since the spinal implant 20 is not externally threaded, forming a cylindrically-shaped passage between and into the adjacent vertebrae $V_U$, $V_L$ and tapping the passage is not required. Accordingly, removal or disruption of vertebral tissue from the upper and lower vertebrae $V_U$, $V_L$ is minimized.

Following preparation of the intervertebral disc space and the upper and lower vertebrae $V_U$, $V_L$, the spinal implant 20 is positioned within the intervertebral disc space via a suitable insertion techniques such as, for example, an impaction or push-in type insertion techniques. Notably, since the spinal implant 20 is not threaded, insertion into the disc space can be accomplished without having to thread or otherwise rotate the spinal implant 20 into position. Additionally, in a preferred embodiment, the spinal implant 20 is inserted into the disc space while in a non-expanded configuration to minimize neural distraction. However, it should be understood that in certain circumstances, it may be desirable to transition the spinal implant 20 to an expanded configuration either before or during insertion in the disc space. In a further embodiment of the invention, the spinal implant 20 may be inserted into the disc space in a minimally invasive manner (i.e., through a small access portal) via the use of endoscopic equipment, a small diameter tube or cannula, or by other suitable minimally invasive surgical techniques. However, it should be understood that other conventional surgical methods and techniques may also be used.

After the spinal implant 20 is inserted in the disc space, the fusion cage 22 is transitioned to an expanded configuration via axially displacing the inner shaft 104 of the instrument 100 in the direction of arrow A (toward the distal end 22b of the fusion cage), which correspondingly displaces the expansion member 24 through the inner chamber 50. As discussed above, axial displacement of the expansion member 24 results in sliding engagement between the expansion member 24 and the branch 32, thereby causing the branch portions 32 to separate or splay apart along each of the transverse axes $T_1$ and $T_2$ to transition the fusion cage 22 to the fully expanded configuration illustrated in FIG. 10. As also discussed above, expansion of the fusion cage 22 along the transverse axis $T_1$ distracts and/or restores/maintains lordosis between the upper and lower vertebrae $V_U$, $V_L$, with the upper vertebral bearing surface 34 being oriented at an angle relative to the lower vertebral bearing surface 36.

When the fusion cage 22 is fully expanded to the configuration illustrated in FIG. 10, the expansion member 24 is securely captured between the retention element 72 and the transverse flanges of the branch portions 32 to lock the expansion member 24 in the proper orientation and position and to securely maintain the fusion cage 22 in the expanded configuration. Although the fusion cage 22 is maintained in the expanded configuration solely via engagement between the expansion member 24 and the branch portions 32, it should be understood that one or more supplemental internal fixation elements are also contemplated for use in association with the fusion cage 22, particularly in instances involving excessive vertebral loading and/or instability. It should also be understood that supplemental external intravertebral fixation elements and/or stabilization techniques may also be used if excessive residual instability is encountered following insertion and expansion of one or more of the spinal implants 20 with the disc space.

Once the fusion cage 22 is fully expanded, a bone growth promoting material 120, such as BMP and a suitable carrier, is injected or otherwise loaded into the inner chamber 50 of the fusion cage 22 to facilitate or promote bone growth from the upper and lower vertebrae $V_U$, $V_L$, through the bone growth openings 80, and into and possibly through the fusion cage 22. Additionally, morselized autograft bone or a similar type of material may be positioned adjacent the expanded fusion cage 22 to further promote fusion.

Figure 11:
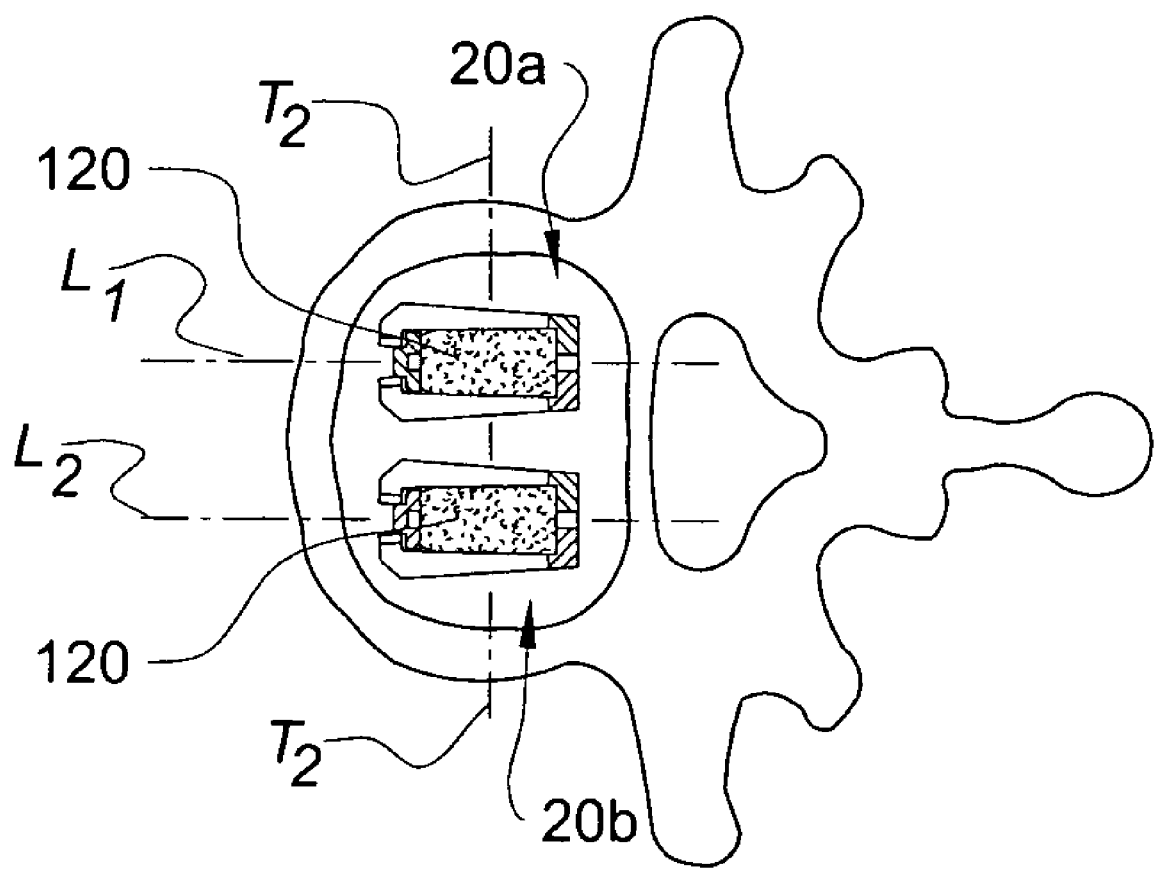
FIG. 11 is a top plan view of a pair fully expanded spinal implants positioned side-by-side in a bi-lateral arrangement within an intervertebral disc space.

In one embodiment of the invention, access to the spinal column and insertion of the spinal implant 20 into the disc space is accomplished via a posterior surgical approach. However, it should be understood that access and insertion of the spinal implant 20 into the disc space may be accomplished via other surgical approaches, such as, for example, an anterior approach or a lateral approach. In another embodiment of the invention, the spinal implant 20 is used to treat the lumbar region of the spine, with the upper and lower vertebrae $V_U$, $V_L$ comprising lumbar vertebrae. However, it should nevertheless be understood that the present invention is also applicable to other portions of the spine, including the cervical, thoracic or sacral regions of the spine. Additionally, as illustrated in FIG. 11, in a further embodiment of the invention, a pair of spinal implants 20a, 20b may be positioned side-by-side in a bilateral arrangement within the disc space. However, it should be understood that unilateral placement or central placement of a single spinal implant 20 within the disc space is also contemplated as falling within the scope of the present invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An expandable spinal implant, comprising:
   a body having a longitudinal axis and an overall length, height and width, said body including a plurality of movable portions extending along said longitudinal axis and cooperating to define a non-threaded outer transverse cross section along said overall length and having a first transverse dimension along said height and a second transverse dimension along said width, said movable portions defining first and second substantially planar outer surfaces disposed generally opposite one another and extending substantially entirely across said width and adapted to engage adjacent vertebral bodies; and
   an expansion member co-acting with said movable portions to expand said outer transverse cross section along each of said first and second transverse dimensions.

2. The implant of claim 1, wherein said movable portions cooperate to define third and forth substantially planar surfaces disposed generally opposite one another and extending between said first and second substantially planar surfaces.

3. The implant of claim 2, wherein said movable portions cooperate to define a generally rectangular outer transverse cross section alone said overall length.

4. The implant of claim 1, wherein said body has a substantially parallelepiped configuration.

5. The implant of claim 1, wherein said first and second substantially planar surfaces are arranged parallel to one another.

6. The implant of claim 1, wherein said first and second substantially planar surfaces extend along one of said first and second transverse dimensions.

7. The implant of claim 1, wherein said first transverse dimension is arranged substantially perpendicular to said second transverse dimension.

8. The implant of claim 1, wherein said movable portions cooperate to define an inner chamber sized to receive said expansion member therein; and
   wherein displacement of said expansion member within said inner chamber engages said expansion member with said movable portions to expand said movable portions along said first and second transverse dimensions.

9. The implant of claim 8, wherein said displacement comprises movement of said expansion member within said inner chamber generally along said longitudinal axis.

10. The implant of claim 9, wherein said movable portions have inner surfaces defining said inner chamber, said inner surfaces defining an inward taper along said longitudinal axis, said expansion member engaging said inner surfaces of said movable portions to expand said body along said first and second transverse dimensions as said expansion member is displaced generally along said longitudinal axis.

11. The implant of claim 10, wherein said inner surfaces of said movable portions are substantially planar.

12. The implant of claim 10, wherein said inner surfaces of said movable portions provide said inner chamber with a substantially rectangular inner cross section.

13. The implant of claim 1, wherein at least one of said movable portions includes a retention element adapted to engage and retain said expansion member in a select position relative to said movable portions upon expansion of said body along said first and second transverse dimensions.

14. The implant of claim 13, wherein said retention element comprises a ridge extending from an inner surface of said one of said movable portions.

15. The implant of claim 14, wherein said retention element comprises a pair of opposing ridges extending from inner surfaces of opposite ones of said movable portions.

16. The implant of claim 14, wherein said retention element further comprises a transverse flange extending inwardly from said inner surface of said one of said movable portions, said expansion member positioned between said retention element and said transverse flange to retain said expansion member in said select position.

17. The implant of claim 1, wherein said movable portions cooperate to define an inner fusion chamber.

18. The implant of claim 17, wherein said first and second substantially planar surfaces each define a plurality of apertures extending therethrough in communication with said inner fusion chamber to facilitate bone growth from the adjacent vertebral bodies and into the fusion chamber.

19. The implant of claim 17, further comprising a bone growth promoting substance disposed within said inner chamber to facilitate fusion with the adjacent vertebral bodies.

20. The implant of claim 19, wherein said bone growth promoting substance comprises a bone morphogenic protein.

21. The implant of claim 1, wherein said first and second substantially planar surfaces define a plurality of anchor elements adapted to engage the implant with the adjacent vertebral bodies.

22. The implant of claim 21, wherein said anchor elements comprise ridges extending generally along a corresponding one of said first and second transverse dimensions and axially spaced along the longitudinal axis.

23. The implant of claim 1, wherein said body is formed of a material having a modulus of elasticity substantially similar to bone.

24. The implant of claim 1, wherein said body is formed of a polymeric material.

25. The implant of claim 24, wherein said polymeric material comprises a composite polymer.

26. The implant of claim 1, wherein said body is formed of a resorbable material.

27. The implant of claim 26, wherein said resorbable material comprises a polymeric material.

28. The implant of claim 1, wherein said body includes a fixed base portion having a constant outer cross section, each of said movable portions depending from said fixed base portion.

29. The implant of claim 28, wherein said movable portions are formed integral with said fixed base portion to define a single-piece unitary body.

30. An expandable spinal implant, comprising:
a body having a longitudinal axis and an overall length, height and width, said body including a plurality of movable portions extending along said longitudinal axis and cooperating to define a generally rectangular, non-threaded outer transverse cross section along said overall length, said body having a first transverse dimension along said height and a second transverse dimension along said width; and
an expansion member co-acting with said plurality of movable portions to expand said outer transverse cross section along each of said first and second transverse dimensions.

31. The implant of claim 30, wherein said body has a substantially parallelepiped configuration.

32. The implant of claim 30, wherein said first transverse dimension is substantially perpendicular to said second transverse dimension.

33. The implant of claim 30, wherein said movable portions cooperate to define an inner chamber sized to receive said expansion member therein; and
wherein displacement of said expansion member within said inner chamber engages said expansion member with said movable portions to expand said movable portions along said first and second transverse dimensions.

34. The implant of claim 33, wherein said displacement comprises movement of said expansion member within said inner chamber generally along said longitudinal axis.

35. The implant of claim 33, wherein said movable portions have substantially planar inner surfaces defining said inner chamber, said inner surfaces defining an inward taper along said longitudinal axis, said expansion member engaging said planar inner surfaces of said movable portions to expand said body along said first and second transverse dimensions as said expansion member is displaced generally along said longitudinal axis.

36. The implant of claim 30, wherein said movable portions cooperate to define an inner fusion chamber for receiving a bone growth promoting substance to facilitate fusion with adjacent vertebral bodies.

37. The implant of claim 30, wherein said movable portions define first and second substantially planar surfaces disposed generally opposite one another and extending substantially entirely across said width and adapted to engage adjacent vertebral bodies, said planar outer surfaces defining a plurality of anchor elements adapted to engage the implant with the adjacent vertebral bodies.

38. The implant of claim 30, wherein said body includes a fixed base portion having a constant outer cross section, each of said movable portions depending from said fixed base portion.

39. The implant of claim 38, wherein said movable portions are formed integral with said fixed base portion to define a single-piece unitary body.

40. An expandable spinal implant, comprising:
a body having a longitudinal axis and an overall length, height and width, said body including and a plurality of movable portions cooperating to define an outer cross section having a first transverse dimension along said height and a second transverse dimension along said width, said movable portions having substantially planar inner surfaces that cooperate to define an inner chamber having a substantially rectangular inner transverse cross section along said overall length, said inner surfaces defining an inward taper along said longitudinal axis; and
an expansion member having a substantially rectangular outer transverse cross section and including substantially planar outer surfaces that engage said substantially planar inner surfaces of said movable portions to expand said movable portions along each of said first and second transverse dimensions as said expansion member is displaced generally along said longitudinal axis.

41. The implant of claim 40, wherein said movable portions cooperate to define a non-threaded outer transverse cross section along said overall length and first and second substantially planar outer surfaces disposed generally opposite one another and extending substantially entirely across said width and adapted to engage adjacent vertebral bodies.

42. The implant of claim 41, wherein said first and second substantially planar outer surfaces are arranged parallel to one another.

43. The implant of claim 41, wherein each of said first and second substantially planar outer surfaces define a plurality of apertures extending therethrough in communication with said inner chamber.

44. The implant of claim 41, wherein said first and second substantially planar outer surfaces define a plurality of anchor elements adapted for engagement with the adjacent vertebral bodies.

45. The implant of claim 40, wherein said movable portions cooperate to define a generally rectangular, non-threaded outer transverse cross section alone said overall length.

46. The implant of claim 45, wherein said body has a substantially parallelepiped configuration.

47. The implant of claim 40, wherein at least one of said movable portions includes a retention element adapted to engage and retain said expansion member in a select position relative to said movable portions upon expansion of said movable portions along said first and second transverse dimensions.

48. The implant of claim 40, further comprising a bone growth promoting substance disposed within said inner chamber to facilitate fusion with adjacent vertebral bodies.

49. An expandable spinal implant, comprising:
a body having a longitudinal axis and an overall length, height and width, said body including a plurality of movable portions extending along said longitudinal axis and cooperating to define a non-threaded outer transverse cross section along said overall length and having a first transverse dimension along said height and a second transverse dimension along said width, said movable portions defining first and second substantially planar outer surfaces disposed generally opposite one another and extending substantially entirely across said width and adapted to engage adjacent vertebral bodies; and means for expanding said outer transverse cross section along said first and second transverse dimensions.

* * * * *